United States Patent [19]
Weiner

[11] Patent Number: 5,297,346
[45] Date of Patent: Mar. 29, 1994

[54] DEVICE FOR MEASURING DISTANCE AND DETERMINING POSITION FROM A REFERENCE POINT, AND METHOD OF USING SAME

[75] Inventor: Mark A. Weiner, New York, N.Y.

[73] Assignee: Irving M. Weiner, Walled Lake, Mich. ; a part interest

[21] Appl. No.: 796,814

[22] Filed: Nov. 25, 1991

[51] Int. Cl.[5] .............................. A61B 1/04; G01B 5/02
[52] U.S. Cl. ........................................ 33/512; 33/747; 33/775
[58] Field of Search ............... 33/714, 715, 716, 719, 33/720, 737, 734, 745, 747, 751, 773, 775, 779, 780, 512, 511

[56] References Cited
U.S. PATENT DOCUMENTS

| | | | |
|---|---|---|---|
| 1,624,633 | 4/1927 | Spoerri | 33/737 |
| 1,695,701 | 12/1928 | Steiner | 33/716 |
| 1,912,485 | 6/1933 | Kothny | 33/775 |
| 1,982,184 | 11/1934 | Williams et al. | 33/747 |
| 2,099,794 | 11/1937 | Bonney et al. | 33/775 |
| 2,383,844 | 8/1945 | Bouslog | 33/747 |
| 3,500,546 | 3/1970 | Pilcher | 33/715 |
| 4,461,015 | 7/1984 | Kulhavy | 33/719 |
| 4,471,656 | 9/1984 | Sanoers et al. | 33/715 |
| 4,860,631 | 8/1989 | Aoshiro | 33/719 |

FOREIGN PATENT DOCUMENTS 0447860 5/1936 United Kingdom ................. 33/737

Primary Examiner—Thomas B. Will
Attorney, Agent, or Firm—Irving M. Weiner; Joseph P. Carrier; Pamela S. Burt

[57] ABSTRACT

An apparatus for determining and indicating the location of an end portion of a probe inserted into an external body. As the probe moves it rotates a measuring wheel to indicate linear translation, and optionally also moves another measuring wheel to indicate angular rotation of the probe. The data representative of probe linear insertion and angular orientation is recorded synchronously on a record for display with data obtained from a transponder positioned near the end portion of the probe.

18 Claims, 1 Drawing Sheet

DEVICE FOR MEASURING DISTANCE AND DETERMINING POSITION FROM A REFERENCE POINT, AND METHOD OF USING SAME

TECHNICAL FIELD

The invention relates generally to a device for measuring distance and determining position from a reference point, and methods of utilizing same. In particular, the invention relates to a device for measuring distance from a reference point in semi-invasive ultrasound and endoscopic procedures, and methods of utilizing same.

BACKGROUND

The art is exemplified by U.S. Pat. No. 3,248,796; 3,318,005; 4,344,428; 4,389,885; 4,481,714; 4,646,752 and U.S. Pat. No. 4,905,698.

Various medical procedures exist whereby a long flexible tube is advanced into a body orifice (e.g., the esophagus or the colon) so that images, either video or ultrasound, can be transmitted to the observer. Once the tube is inserted into the orifice, it is often difficult to judge distance properly. Recently, the medical profession is requiring more and more precise measurements of endoscopic and ultrasonographic procedures for either the staging of pathological lesions or research protocols.

The present invention provides an apparatus which will measure the precise distance a probe has been inserted into an orifice, and transmit that data to a recording instrument or other associated devices. The invention is not limited to medical procedures, and can be used in a host of other applications.

SUMMARY OF THE INVENTION

The term "elongated device" as used herein is intended in its broadest sense, and includes, but is not limited to, probes, drilling devices, cutting devices, optical fibers, pipes, and tubes, and any and all of the foregoing items with or without a transponder, a manipulating or surgical device or any other "utility device" as defined herein, located at a predetermined portion of the elongated device.

The term "utility device" as used herein is intended in its broadest sense, and includes, but is not limited to, any device which senses or detects by way of light, infrared light, ultraviolet light, fiber optics, sound, ultrasound, X-rays, electromagnetic waves, chemical or biological phenomena, or pressure; surgical devices; devices which treat by way of spraying, manipulation, pressure, and injection; devices which cut, drill, puncture, or implant; and devices which radiate, cleanse or irrigate.

The term "external body" as used herein and is intended in its broadest sense, and includes, but is not limited to, the human body, animal bodies, the Earth, any body of water, any terrain, and any object which is external to the inventive apparatus.

The invention provides an apparatus for determining and indicating the location of a predetermined portion of an elongated device within an external body, and comprises first means for permitting at least a portion of the elongated device to move therethrough and for sensing movement of the elongated device. Second means, operably connected to the first means, determines and indicates the location of the predetermined portion of the elongated device relative to a selected zero point. Third means, operably connected to the second means, is used for selecting the zero point.

The invention also provides a method for determining and indicating the location of a predetermined portion of an elongated device within an external body, comprising the steps of: releasably and adjustably securing an apparatus to a predetermined portion of said external body; moving said elongated device through said apparatus and into said external body; sensing movement of said elongated device as it moves through said apparatus; selecting a zero point for said elongated device; and determining and indicating the location of said predetermined portion of said elongated device relative to said selected zero point.

DETAILED DESCRIPTION

Figure 1:
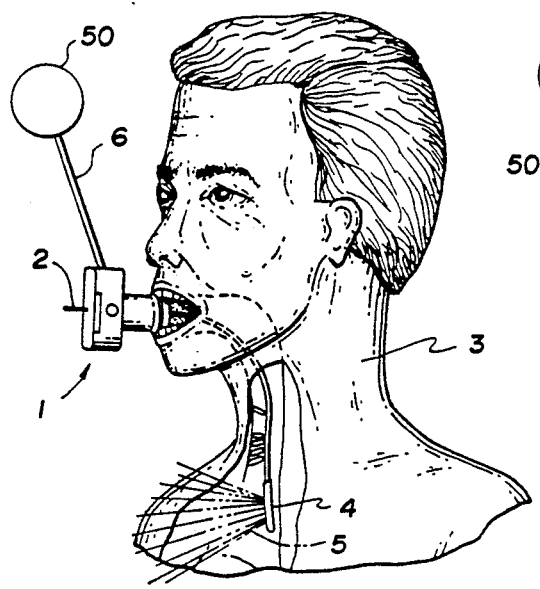
FIG. 1 is a perspective view showing the inventive apparatus in use via the human mouth.

FIG. 1 shows the inventive apparatus 1 through which an elongated device, preferably but not necessarily in the form of an ultrasound or endoscopic probe 2, passes through into an external body, such as a human patient 3. At a predetermined portion of probe 2 there may be preferably but not necessarily provided a utility device, such as an ultrasound transponder 4.

The ultrasonic transponder 4 may provide an ultrasound fan view 5, the signals for which are transmitted through the probe 2 to a recording/display device 50, preferably but not necessarily such as a VCR. Electrical signals from the apparatus I representative of location and distance of the transponder 4 are transmitted via conductors 6 to recording/display device 50 for recording and display in synchronism with the ultrasonic picture. Thus, the transponder 4 and its ultrasonic fan view 5 are precisely located within the anatomical structure of the body.

Figure 2:
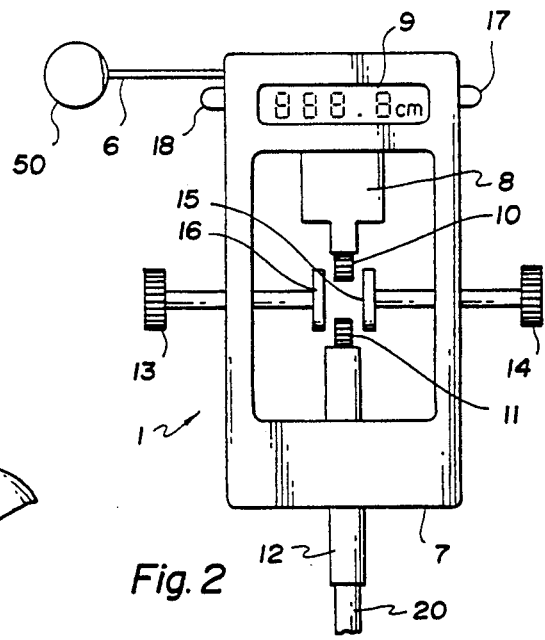
FIG. 2 is a top plan view of a first embodiment of the invention which measures linear translation of the elongated device.
Figure 3:
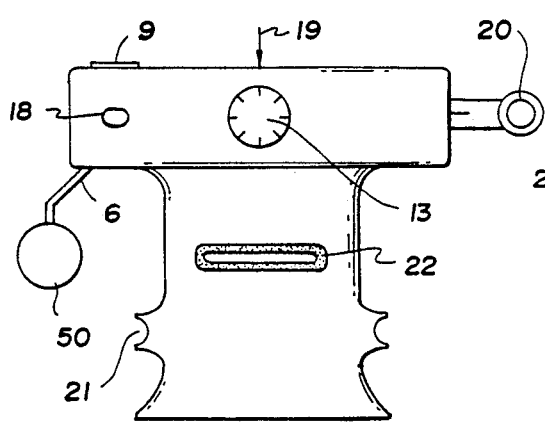
FIG. 3 is a side view of the first embodiment.
Figure 4:
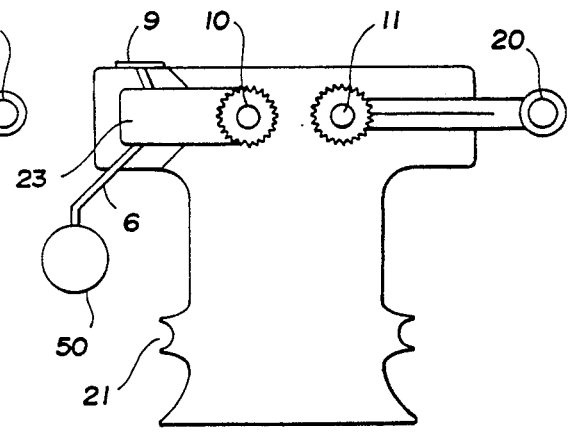
FIG. 4 is a side sectional view of the first embodiment.

FIGS. 2-4 represent a first embodiment of the invention. The top view shown in FIG. 2 shows that the apparatus 1 has a housing structure 7 provided with a measuring device housing 8 and a display 9. The measuring wheel 10 is operably connected to the measuring device housing 8 which encloses the mechanical/electronic device 23 (FIG. 4) for converting rotations of the measuring wheel 10 into electronic signal representative of distance of travel of the probe 2. Suitable devices, such as potentiometers, are known for converting mechanical rotation into analogue electrical signals, and for converting analogue signals to digital signals.

Diametrically opposed to the measuring wheel 10 is preferably but not necessarily an opposing traction wheel 11 to urge the probe 2 into contact with measuring wheel 10. Opposing traction wheel 11 is preferably but not necessarily operably connected to preferably but not necessarily a sliding bar 12 to adjustably lock the traction wheel left in place.

Apparatus 1 is preferably but not necessarily also provided with probe stabilizers 15 and 16 which are each associated with preferably but not necessarily a threaded adjustable probe-stabilizing screw or knob 13 and 14, respectively. The probe 2 is inserted between measuring wheel 10, opposing traction wheel 11, and probe stabilizers 15 and 16. As the probe 2 moves, it rotates the measuring wheel 10 which generates an electrical signal indicative of the distance which the probe 2 has moved. Should the probe 2 be retracted (upwardly as shown in FIG. 3), the direction of rotation of measuring wheel reverses, and an incremental negative distance signal is generated by device 23 within measuring device housing 8.

The distance traveled by probe 2 is preferably but not necessarily displayed on display 9, which can preferably but not necessarily be selectively reset to zero by way of the zero button 17. In addition to the display 9, electronic signals indicative of the movement of probe 2 are sent to the recording/display device 50 by way of conductor 6. In addition to the signals representative of the distance probe 2 has traveled, the user may preferably but not necessarily selectively use a marking button 18 to generate and record on the same record various marking points, such as anatomical landmarks, reference points, or desired distance reference points.

The side view of the FIG. 2 device as shown in FIG. 3 includes a reference arrow 19 for indicating the insertion direction of probe 2. There is also shown a handle 20 which is preferably but not necessarily operably connected to slide bar 12 to adjustably position and lock in place traction wheel 11.

When the device is used for placing an end thereof in the patient's mouth (FIG. 1), there is preferably but not necessarily provided a bite guard 21 as shown in FIGS. 3 and 4. Loops 22 may preferably but not necessarily be provided on both sides of apparatus I to accommodate a stabilizing strap (not shown) which goes around the patient's head to further stabilize the apparatus device and to selectively and releasably secure the apparatus to the patient.

The sectional view in FIG. 4 also shows the electronic measuring device 23 which is enclosed within measuring device housing 8.

Figure 5:
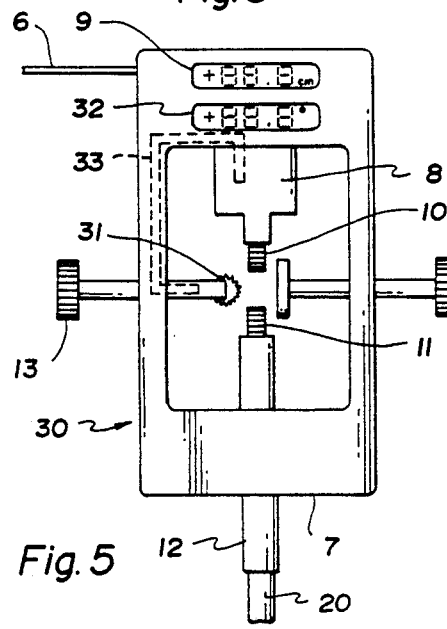
FIG. 5 is a top plan view of a second embodiment of the invention which has a linear measuring wheel as well as a separate angular measuring wheel.

FIG. 5 shows a second embodiment of the invention, in which components similar to the first embodiment are designated by like reference numerals. In addition to the elements described hereinabove with reference to the first embodiment, the apparatus 30 is preferably but not necessarily provided with an angular measuring wheel 31 to sense and measure angular movement of the probe 2. The data and information detected by angular measuring wheel 31 is conveyed via conductors 33 to the electronic measuring device 23 within measuring device housing 8. The data representative of angular movement of probe 2 is displayed on display 32 indicating angular rotation. Thus, apparatus 30 has a linear measuring wheel 10 for detecting linear translation of probe 2, and a separate angular measuring wheel 31 for detecting angular rotation of probe 2. In this manner, the precise distance and angular orientation of the utility device, such as transponder 4, within the external body, such as patient 3, can be detected, measured, and recorded and/or displayed along with the information detected by transponder 4.

The invention also contemplates means for contactless measurement of angular rotation as disclosed in U.S. Pat. No. 5,027,067 which is incorporated herein by reference thereto.

Figure 6:
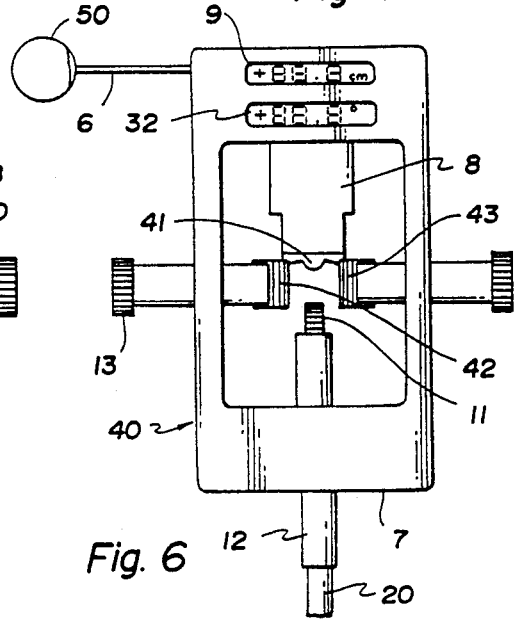
FIG. 6 is a top plan view of a third embodiment of the invention which has a textured track-ball for sensing movement of the elongated device in all directions.

FIG. 6 shows a third embodiment of the invention, wherein components common to the first and second embodiments are designated by like numerals. The apparatus 40 is preferably but not necessarily provided with a textured track-ball 41 which rotates in any and all directions, and provides detected angular and linear movement of probe 2 to the electronic measuring device 23 within the measuring device housing 8. Thus, apparatus 40 provides information representative of linear translation as well as angular rotation of the probe 2 with a common measuring device, such as preferably but not necessarily the textured track-ball 41.

The apparatus 40 is preferably but not necessarily also provided with side stabilizing wheels 42 and 43 which replace probe stabilizers 16 and 15, respectively, shown in FIG. 2.

With reference to apparatus 40, in order to accommodate for various probe diameters, the apparatus is provided with a calibration wheel (not shown). As an alternative, calibration may be integrated into device 23 and/or the software in the recording device 50. The recording/display device 50 may be uncorporated with a computer, or electrically connected thereto.

In FIGS. 5 and 6, the zero button 17 and the marking button 18 have been omitted for clarity.

In use, the probe 2 may preferably but not necessarily be inserted into the apparatus and moved to a desired point on the external body, such as the teeth of the patient, at which point the zero button is actuated resetting the display 9 to zero. As the probe 2 goes further into the body, the information displayed via the transponder 4 is synchronously displayed with the distance from the zero point. The user is also given the option to use the marking button 18 to designate various body or anatomical landmarks.

It will be apparent to the artisan that the inventive apparatus can be used on various portions of the human body, and various orifices thereof, and can also be used on and in any external object or body.

While three embodiments of the invention have been disclosed, many modifications will be apparent and it is intended that the invention be interpreted as including all modifications which fall within the true spirit and scope of the invention as set forth in the appended claims.

I claim:

1. Apparatus for determining and indicating a location of a predetermined portion of an elongated device within a living organism, comprising, in combination:

first means for permitting at least a portion of said elongated device to move therethrough into said living organism for sensing movement of said elongated device;

second means connected to said first means for determining and indicating distance and location of said predetermined portion of said elongated device within said living organism relative to a selected zero point;

third means connected to said second means for selecting said zero point;

an ultrasound transponder at said predetermined portion of said elongated device for providing an ultrasonic picture of anatomical features within said living organism; and fourth means connected to said ultrasound transponder and said first, second and third means for recording and displaying signals representative of the location and distance of said predetermined portion of said elongated device within said living organism relative to said selected zero point in synchronism with said ultrasonic picture of anatomical features within said living organism in the vicinity of said predetermined portion of said elongated device.

2. Apparatus according to claim 1, wherein:
said first means senses linear translation as well as angular movement of said elongated device.

3. Apparatus according to claim 1, wherein:
said first means senses linear translational movement of said elongated device.

4. Apparatus according to claim 1, wherein:
said first means senses angular movement of said elongated device.

5. Apparatus according to claim 1, including:
fifth means connected to said second means for marking and indicating one or more anatomical landmarks which are located within said living organism; and
sixth means connected to said first means for adjustably stabilizing said elongated device as it moves through said first means.

6. Apparatus according to claim 2, wherein:
said first means includes at least one linear measuring wheel and at least one angular measuring wheel.

7. Apparatus according to claim 5, wherein said second and fourth means include:
seventh means connected to said first means for visually indicating linear distance through which said elongated device has moved; and
eighth means connected to said first means for visually indicating angular rotation of said elongated device.

8. Apparatus for determining and indicating a location of a predetermined portion of an elongated device within a living organism, comprising, in combination;
first means for permitting at least a portion of said elongated device to move therethrough into said living organism and for sensing movement of said elongated device;
second means connected to said first means for determining and indicating distance and location of said predetermined portion of said elongated device within said living organism relative to selected zero point;
third means connected to said second means for selecting said zero point;
an ultrasound transponder at said predetermined portion of said elongated device for providing an ultrasonic picture of anatomical features within said living organism; and
fourth means connected to said ultrasound transponder and said first, second and third means for recording and displaying signals representative of the location and distance of said predetermined portion of elongated device within said living organism in synchronism with said ultrasonic picture of anatomical features within said living organism in the vicinity of said predetermined portion of said elongated device; and
fifth means connected to said second and fourth means for marking and indicating one or more anatomical landmarks which are located within said living organism.

9. Apparatus according to claim 8, wherein:
said first means senses linear translation as well as angular movement of said elongated device.

10. Apparatus according to claim 8, wherein:
said first means senses linear translational movement of said elongated device.

11. Apparatus according to claim 8, wherein:
said first means senses angular movement of said elongated device.

12. Apparatus according to claim 8 including:
sixth means connected to said first means for adjustably stabilizing said elongated device as it moves through said first means;
seventh means connected to said second and fourth means for displaying linear distance said elongated device has moved within said living organism;
eighth means connected to said second and fourth means for displaying angular rotation of said elongated device; and
ninth means connected to said first means for selectively and releasably affixing said apparatus to a predetermined portion of said living organism.

13. Apparatus according to claim 12, wherein:
said first means includes a rotatable measuring wheel; and
including tenth means connected to said first means for adjustably urging said elongated device into contact with said measuring wheel.

14. A method for determining and indicating a location of a predetermined portion of an elongated device within a living organism, comprising the steps of:
releasably and adjustably securing an apparatus to a predetermined portion of said living organisms;
moving said elongated device through said apparatus and into said living organism;
sensing movement of said elongated device as it moves through said apparatus and within said living organism;
selecting a zero point for said elongated device;
determining and indicating the location of said predetermined portion of said elongated device relative to said zero point;
generating an ultrasonic picture of anatomical features with said living organism; and
displaying electrical signals representative of the location of said predetermined portion of said elongated device within said living organism in synchronism with said ultrasonic picture of anatomical features within said living organism in the vicinity of said predetermined portion of said elongated device.

15. Method according to claim 14, including the step of:
marking and indicating one or more anatomical landmarks which are located within said living organism.

16. Method according to claim 14, including the steps of:
displaying the linear distance and predetermined portion of said elongated device has traveled relative to said selected zero point; and
separately displaying the angular rotation of said predetermined portion of said elongated device relative to said selected zero point.

17. Method according to claim 14, including the step of:
adjustably stabilizing said elongated device as it moves through said apparatus.

18. Method according to claim 14 including the step of:
urging said elongated device into contact with the movement sensing element of said apparatus and said elongated device passes through apparatus.

* * * * *

UNITED STATES PATENT AND TRADEMARK OFFICE
CERTIFICATE OF CORRECTION

PATENT NO. : 5,297,346
DATED : March 29, 1994
INVENTOR(S) : Mark A. Weiner

It is certified that error appears in the above-indentified patent and that said Letters Patent is hereby corrected as shown below:

Column 2, line 45, change "apparatus I" to --apparatus 1--.
Column 3, line 20, after "9," insert --the--;
Column 3, line 40, change "apparatus I" to --apparatus 1--.
Column 4, line 25, change "recording" to --recording/display--.
Column 5, line 48 (claim 8, line 11), after "to" insert --a--.
Column 6, line 66 (claim 18, line 4), change "and" to --as--.

Signed and Sealed this

Ninth Day of August, 1994

*Attest:*

BRUCE LEHMAN

*Attesting Officer*  *Commissioner of Patents and Trademarks*